（12） United States Patent
Sagisaka et al.

(10) Patent No.: US 8,815,957 B2
(45) Date of Patent: Aug. 26, 2014

(54) SURFACTANT

(75) Inventors: Masanobu Sagisaka, Hirosaki (JP); Shuho Iwama, Hirosaki (JP); Masahiro Hida, Funabashi (JP); Yasufumi Shikauchi, Funabashi (JP)

(73) Assignees: Nissan Chemical Industries, Ltd., Tokyo (JP); Hirosaki University, Aomori (JP)

( * ) Notice: Subject to any disclaimer, the term of this patent is extended or adjusted under 35 U.S.C. 154(b) by 363 days.

(21) Appl. No.: 13/038,867

(22) Filed: Mar. 2, 2011

(65) Prior Publication Data
US 2012/0049111 A1  Mar. 1, 2012

(30) Foreign Application Priority Data

Sep. 1, 2010  (JP) ................................. 2010-195750

(51) Int. Cl.
*B01F 17/10* (2006.01)
*C07C 309/17* (2006.01)
*C07C 303/06* (2006.01)
*B01F 3/04* (2006.01)
*B01F 3/08* (2006.01)

(52) U.S. Cl.
CPC ............ *C07C 309/17* (2013.01); *Y10S 516/909* (2013.01)
USPC ................................ 516/9; 516/200; 516/909

(58) Field of Classification Search
CPC ... C07C 309/17; C07C 303/06; B01F 3/0092; B01F 17/0035; B01F 17/0057; C09K 3/00
USPC ........................ 516/9, 200, 909; 560/190, 197
See application file for complete search history.

(56) References Cited

U.S. PATENT DOCUMENTS

| 8,263,800 B2 * | 9/2012 | Murphy et al. ............... 510/489 |
| 2010/0003737 A1 * | 1/2010 | Murphy et al. ............... 516/203 |

(Continued)

FOREIGN PATENT DOCUMENTS

| GB | 1 467 988 | * | 3/1977 |
| JP | 2004-258096 | * | 9/2004 |

(Continued)

OTHER PUBLICATIONS

Sagisaka et al, "Preparation and Application of Organic Solvent-Free Supercritical Carbon Dioxide Microemulsions", Journal of the Japan Society of Colour Material, vol. 83 (Feb. 2010) No. 2, pp. 66-75.*

(Continued)

*Primary Examiner* — Daniel S Metzmaier
(74) *Attorney, Agent, or Firm* — Oliff PLC

(57) ABSTRACT

A surfactant for water/supercritical carbon dioxide microemulsions that can achieve high water dispersion ability, water/supercritical carbon dioxide microemulsion forming ability under a moderate condition, and high water solubilization rate and that reduces burden on the environment and ecosystem. Provided are a surfactant for stabilizing a water/supercritical carbon dioxide microemulsion including a compound of Formula (I) and a water/supercritical carbon dioxide microemulsion including the surfactant. The compound of Formula (I) has the structure:

(1)

$$\text{R}_f\text{CH}_2\text{CH}_2\text{O} - \overset{\overset{\displaystyle O}{\|}}{\underset{}{\text{C}}} - \text{CH}(\text{SO}_3\text{M}) - \text{CH}_2 - \overset{\overset{\displaystyle O}{\|}}{\underset{}{\text{C}}} - \text{OCH}_2\text{CH}_2\text{R}_f$$

5 Claims, 5 Drawing Sheets

(56) References Cited

U.S. PATENT DOCUMENTS

2010/0004482 A1* 1/2010 Murphy et al. ............... 560/192
2013/0023687 A1* 1/2013 Sagisaka et al. ............... 558/38

FOREIGN PATENT DOCUMENTS

JP    A-2004-315675    11/2004
JP    2007-237617 A *  9/2007

OTHER PUBLICATIONS

Sagisaka et al, "Preparation and Application of Organic Solvent-Free Supercritical Carbon Dioxide Microemulsions", Journal of the Japan Society of Colour Material, vol. 83 (2010) No. 2, pp. 66-75, online @ https://www.jstage.jst.go.jp/browse/shikizai/83/2/_contents.*

Sagisaka et al, "Optimum Tail Length of Fluorinated Double-Tail Anionic Surfactant for Water/Supercritical CO2 Microemulsion Formation", Langmuir, vol. 23, Issue 17(Aug. 14, 2007), pp. 8784-8788.*

Eastoe et al, "Effects of Fluorocarbon Surfactant Chain Structure on Stability of Water-in-Carbon Dioxide Microemulsions. Links between Aqueous Surface Tension and Microemulsion Stability", Langmuir, 2002, 18, pp. 3014-3017.*

Machine Translation of Publ. No. JP 2007-237617, published Sep. 2007, Japan patent Office, Tokyo, Japan, obtained online @ http://dossier1.ipdl.inpit.go.jp/AIPN/odse_top_dn.ipdl?N0000=7400 (Downloaded Nov. 28, 2013).*

Otake et al., "Effective Dispersion of Water into Supercritical Carbon Dioxide," *Hyomen* (Surface), 2002, pp. 9-23, vol. 40, No. 10 (w/ English abstract).

Ed. Adschiri, "Nano Technology with Supercritical Fluids," *Microemulsion and Nanomaterials*, Aug. 2004, Ch. 3, Sect. 5, CMC Publishing (w/ English abstract).

Ryoo et al., "Water-in-Carbon Dioxide Microemulsions with Methylated Branched Hydrocarbon Surfactants," *Ind. Eng. Chem. Res.*, 2003, pp. 6348-6358, vol. 42, American Chemical Society.

Holmes et al., "Synthesis of Cadmium Sulfide Q Particles in Water-in-$CO_2$ Microemulsions," *Langmuir*, Aug. 31, 1999, pp. 6613-6615, vol. 15, American Chemical Society.

Harrison et al., "Water-in-Carbon Dioxide Microemulsions with a Fluorocarbon-Hydrocarbon Hybrid Surfactant," *Langmuir*, 1994, pp. 3536-3541, vol. 10, American Chemical Society.

Eastoe et al., "Water-in-$CO_2$ Microemulsions Studied by Small-Angle Neutron Scattering," *Langmuir*, 1997, pp. 6980-6984, vol. 13, American Chemical Society.

Liu et al., "Water in Carbon Dioxide Microemulsions with Fluorinated Analogues of AOT," *Langmuir*, Dec. 29, 2000, pp. 274-277, vol. 17, American Chemical Society.

Sagisaka et al., "Preparation of a W/sc$CO_2$ Microemulsion Using Fluorinated Surfactants," *Langmuir*, Dec. 21, 2002, pp. 220-225, vol. 19, American Chemical Society.

Sagisaka et al., "Novel fluorinated double-tail surfactant having high microemulsifying ability in water/supercritical $CO_2$ system," *J. of Supercritical Fluids*, 2010, pp. 131-136, vol. 53, Elsevier B.V.

Sagisaka et al., "Self-organization Behavior of Surfactants in Supercritical Carbon Dioxide," *Oleoscience*, 2010, pp. 167-177, vol. 10, No. 5, Japan Oil Chemists' Society (w/ English abstract).

* cited by examiner

SURFACTANT

DETAILED DESCRIPTION OF THE INVENTION

1. Technical Field

The present invention relates to a surfactant, and more specifically, relates to a surfactant for stabilizing a water/supercritical carbon dioxide microemulsion.

2. Related Art

Supercritical carbon dioxide (hereinafter may also be called $scCO_2$) is a fluid of carbon dioxide formed at a critical temperature (31.1° C.) and a critical pressure (73.8 bar) or more. $ScCO_2$ is expected as an environmentally friendly alternative solvent because it has characteristics comparatively similar to those of nonpolar solvents such as hexane. For example, a thermodynamically stable water/supercritical carbon dioxide microemulsion (hereinafter may also be called W/$scCO_2$ µE) in which water (hereinafter also called W) or the like is dispersed as fine drops of a nanometer level in $scCO_2$ is expected to be applied to various fields such as dry-cleaning, extraction of useful components including metal ions and proteins, and reaction fields for organic synthesis and particle synthesis.

A surfactant that can be dissolved in $scCO_2$ is required for forming the W/$scCO_2$ µE, and various surfactants have been studied until now.

For example, typical examples of hydrocarbon surfactants include AOT (Aerosol-OT [registered trademark]: sodium bis-2-ethyl-1-hexylsulfosuccinate). However, AOT is not dissolved in $scCO_2$ at all or, even when a microemulsion if formed, its $W_0^c$ (value showing the number of water molecules that can be solubilized (dispersed) based on one molecule of a surfactant) is up to 10 (Non-patent Document 1, page 12, lines 35 to 41). Thus, AOT is considered to be unsuitable as a surfactant for W/$scCO_2$ µE.

A known hydrocarbon surfactant effective for W/$scCO_2$ µE is a polyoxyethylene surfactant having a multibranched alkyl chain and having a $W_0^c$ of about 20, TMN-6 (Tergitol [registered trademark]: polyethylene glycol trimethylnonyl ether) (Non-patent Document 2, page 112, lines 19 to 29, or Non-patent Document 3).

However, the hydrocarbon surfactant, TMN-6, has problems, that is, TMN-6 requires high pressure for forming a W/$scCO_2$ µE (a pressure at least 100 atmospheres higher than that for a fluorocarbon surfactant described later), and when water is introduced more than a $W_0^c$ value of TMN-6, even a formed W/$scCO_2$ µE cannot be stabilized to separate into two phases.

In contrast, fluorocarbon compounds are known to be well dissolved in $scCO_2$ (Patent Document 1).

Examples of the fluorocarbon compound include a one-chain type ammonium carboxylate having a $CO_2$-philic perfluoropolyether (PFPE) chain, $PFPECOONH_4$, (Non-patent Document 4) and, as two-chain type fluorocarbon surfactants having two bulky $CO_2$-philic chains, a hybrid surfactant $F_7H_7$ having a fluorocarbon (perfluoroalkyl) chain and a hydrocarbon chain (Non-patent Document 5) and di-$HCF_4$ having two fluorooctyl chains and having a structure similar to that of Aerosol-OT (Non-patent Document 6 or Non-patent Document 7). $PFPECOONH_4$ has a $W_0^c$ value of about 15, $F_7H_7$ has a $W_0^c$ value of about 32, and di-$HCF_4$ has a $W_0^c$ value of about 20. However, there are problems for forming the W/$scCO_2$ µE, in which $F_7H_7$ is readily hydrolyzed at ambient temperature and pressure and di-$HCF_4$ requires a high pressure almost equal to that for the hydrocarbon surfactant as described above.

In contrast, it is reported that a fluorocarbon surfactant having $C_8$ perfluoroalkyl chains as a hydrophobic group: $8FS(EO)_2$ (Non-patent Document 8) has a $W_0^c$ value of about 32 and that a fluorocarbon surfactant having a similar skeleton and having $C_8$ perfluoroalkyl chains as a hydrophobic group: $8FG(EO)_2$ (Non-patent Document 9) can disperse water to a $W_0^c$ of about 70 that conventional surfactants for W/$scCO_2$ µE cannot achieve.

On the other hand, a fluorocarbon surfactant having $C_6$ perfluoroalkyl chains as a hydrophobic group: $6FS(EO)_2$ has a $W_0^c$ value of about 16, which is half the $W_0^c$ value (about 32) of $8FS(EO)_2$ having $C_8$ perfluoroalkyl chains. The fluorocarbon surfactants are ascertained to have a tendency that when a perfluoroalkyl group has a smaller number of carbon atoms, the $W_0^c$ value becomes smaller, that is, a surfactant has an extremely decreased water dispersion ability (Non-patent Document 10).

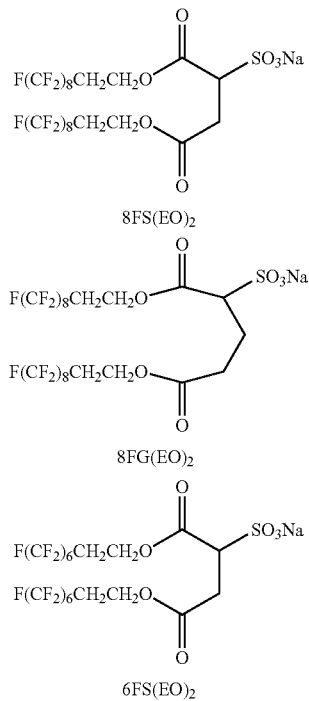

In this manner, when more water molecules, for example, 60 or more of water molecules are dispersed with respect to a molecule of a surfactant, it is considered that a compound having perfluoroalkyl groups having a carbon atom number of 8 or more is effectively used.

However, a compound having perfluoroalkyl groups having a carbon atom number of 8 or more gives burden on the environment and ecosystem and the use of such compound is limited by the regulations on perfluorooctanoic acid (PFOA) and perfluorooctanesulfonic acid (PFOS).

SUMMARY OF THE INVENTION

Problem to be Solved by the Invention

As mentioned above, conventionally developed hydrocarbon surfactants have high solubility in water but poor affinity for $CO_2$ and thus do not have enough ability for dispersing a large amount of water. Even when a surfactant can form a W/$scCO_2$ µE, the surfactant requires high pressure for forming a μE, and when water is introduced more than a $W_0^c$ value of the surfactant, the formed μE cannot stably be maintained.

In contrast, fluorocarbon surfactants having perfluoroalkyl groups having a carbon atom number of 8 or more are extremely effective as a surfactant for W/scCO$_2$ μE but have a problem of limited use due to the regulations on PFOA and PFOS.

In addition to such problems, the time required to disperse water as nano-drops in a surfactant/CO$_2$ solution is at least several tens of minutes after mixing water even when using such previously developed surfactant having high performance. There has been no report until now on effective surfactants that can form a W/scCO$_2$ μE within several minutes in a continuous industrial process using a W/scCO$_2$ μE.

In view of the above, it is an object of the present invention to provide a surfactant for W/scCO$_2$ μE that can achieve high water dispersion ability, W/scCO$_2$ μE forming ability under moderate conditions, and high water solubilization rate and that reduces burden on the environment and ecosystem.

Means for Solving the Problem

The inventors of the present invention have carried out intensive studies in order to solve the above problems, and as a result, have found that a compound having perfluoroalkyl groups having a carbon atom number of 7 or less surprisingly achieves a high $W_0^c$ value and is useful as a surfactant for W/scCO$_2$ μE, and the present invention has been accomplished.

That is, as a first aspect, the present invention relates to a surfactant for stabilizing a water/supercritical carbon dioxide microemulsion. The surfactant includes a compound of Formula (1):

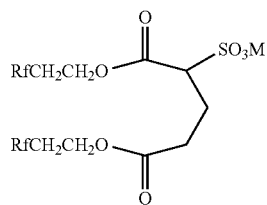

(1)

(where Rf is a $C_{1-7}$ perfluoroalkyl group, and M is a hydrogen atom, an alkali metal, ammonium, a basic amino acid residue, an alkanolamine residue having a $C_{2-3}$ hydroxyalkyl group, or an aliphatic alkanolammonium).

As a second aspect, the present invention relates to the surfactant according to the first aspect, characterized in that the perfluoroalkyl group has a carbon atom number of 1 to 6.

As a third aspect, the present invention relates to the surfactant according to the first aspect, characterized in that the perfluoroalkyl group has a carbon atom number of 4.

As a fourth aspect, the present invention relates to the surfactant according to the first aspect, characterized in that M is an alkali metal.

As a fifth aspect, the present invention relates to a water/supercritical carbon dioxide microemulsion including the surfactant as described in any one of the first aspect to the fourth aspect. In the water/supercritical carbon dioxide microemulsion, the surfactant has a concentration of $10^{-10}$% by mol to $10^2$% by mol based on a molar amount of the supercritical carbon dioxide.

As a sixth aspect, the present invention relates to the water/supercritical carbon dioxide microemulsion according to the fifth aspect, in which the amount of the water (molar ratio ($W_0$)) is 0.001 to 1,000 mol with respect to 1 mol of the surfactant under a condition with a temperature of 75° C. and a pressure of 30 MPa.

EFFECTS OF THE INVENTION

The surfactant of the present invention can provide a remarkably improved water dispersion ability of the surfactant as compared with conventional fluorocarbon surfactants for W/scCO$_2$ μE. Specifically, in the surfactant of the present invention, the perfluoroalkyl group that is a hydrophobic group and provides carbon dioxide-philic properties has a shorter carbon chain, but the surfactant has a water dispersion ability that is almost equal to that of a fluorocarbon surfactant having a longer perfluoroalkyl group. In particular, the surfactant of the present invention shows a water dispersion ability almost equal to that of 8FG(EO)$_2$ having perfluorooctyl groups, which shows the highest water dispersion ability among previously reported surfactants, and has a high water dispersion rate, and thus can reduce the time for forming a W/scCO$_2$ μE from several tens of minutes that a conventional surfactant has required to several seconds to several tens of seconds. Therefore, the surfactant of the present invention is suitably used as a surfactant for W/scCO$_2$ μE and has an advantage in development of a continuous reaction process using a W/scCO$_2$ μE.

Furthermore, the surfactant of the present invention includes a $C_{1-7}$ perfluoroalkyl group, does not include a perfluoroalkyl group having a carbon atom number of 8 or more, which is limited in use due to adverse effects on the environment and ecosystem, and thus is suitably used in industry.

EMBODIMENT(S) OF THE INVENTION

Figure 1:
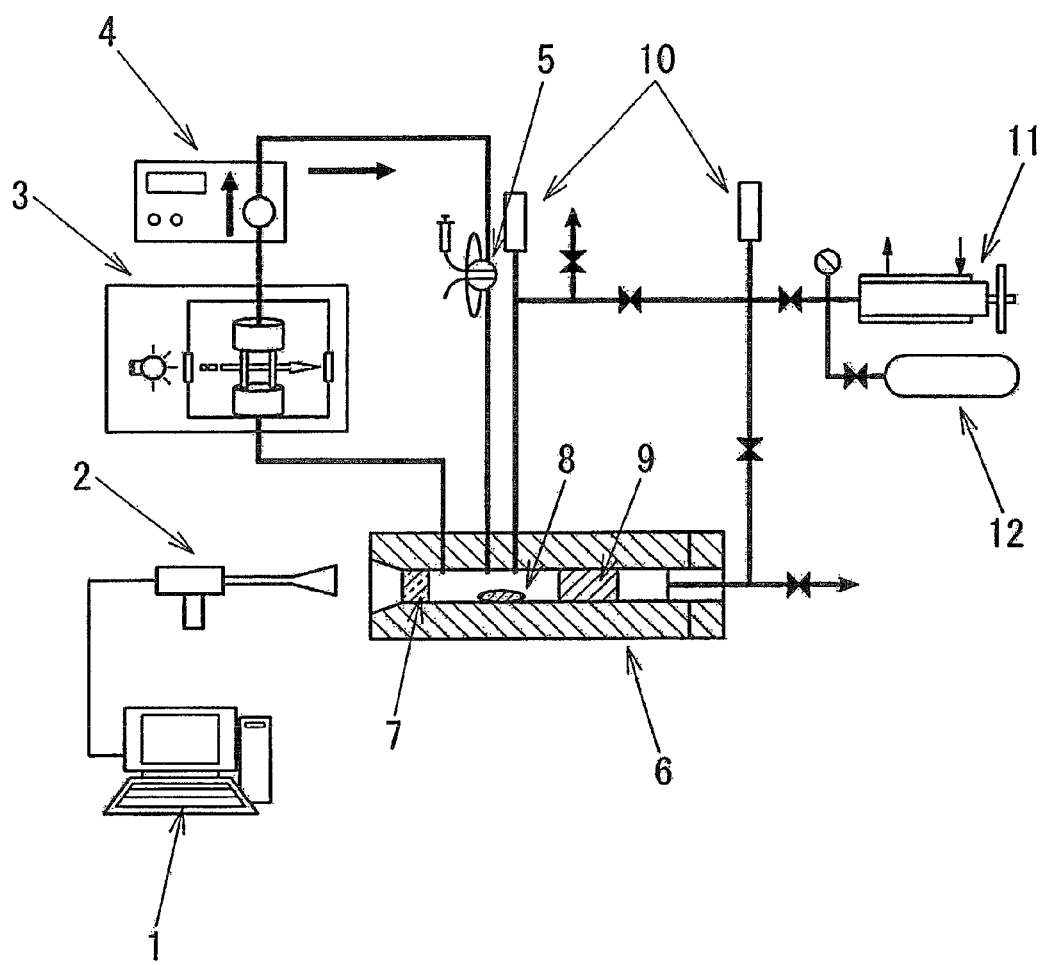
FIG. 1 is a schematic view showing an apparatus used for the phase behavior observation of a water/supercritical carbon dioxide/surfactant mixture in each of Examples 2 and 3 and Comparative Examples 2 and 3.

Hereinafter, the present invention will be described in detail.

In the present specification, $W_0^c$ is a value showing the number of water molecules that can be solubilized (dispersed) based on one molecule of a surfactant. Specifically, $W_0^c$ is the value obtained by dividing the value that is obtained by subtracting the number of moles of water dissolved in carbon dioxide from the total number of moles of water in a system by the total number of moles of a surfactant in the system. $W_0^c$ is an index of a microemulsion forming ability (water dispersion ability) of a surfactant in $scCO_2$.

The present invention relates to a surfactant that includes a compound having perfluoroalkyl groups (fluorocarbon chains) of Formula (1) below and that can disperse water in supercritical carbon dioxide to form and stabilize a water/supercritical carbon dioxide microemulsion.

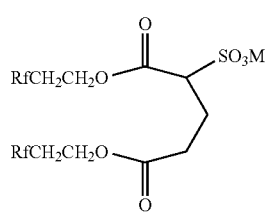

(1)

In Formula (1), Rf is a $C_{1-7}$ perfluoroalkyl group, and M is a hydrogen atom, an alkali metal, ammonium, a basic amino acid residue, an alkanolamine residue having a $C_{2-3}$ hydroxyalkyl group, or an aliphatic alkanolammonium.

Examples of the $C_{1-7}$ perfluoroalkyl group include a perfluoroheptyl group, a perfluorohexyl group, a perfluoropentyl group, a perfluorobutyl group, a perfluoropropyl group, a perfluoroethyl group, a perfluoromethyl group, a perfluoroisoheptyl group, a perfluoroisohexyl group, a perfluoroisopentyl group, a perfluoroisobutyl group, a perfluorocycloheptyl group, a perfluorocyclohexyl group, a perfluorocyclopentyl group, and a perfluorocyclobutyl group. Among them, preferred are $C_{1-6}$ perfluoroalkyl groups such as a perfluorohexyl group, a perfluoropentyl group, a perfluorobutyl group, a perfluoropropyl group, a perfluoroethyl group, a perfluoromethyl group, a perfluoroisohexyl group, a perfluoroisopentyl group, a perfluoroisobutyl group, a perfluorocyclohexyl group, a perfluorocyclopentyl group, and a perfluorocyclobutyl group. Further preferred are $C_4$ perfluoroalkyl groups such as a perfluorobutyl group, a perfluoroisobutyl group, and a perfluorocyclobutyl group.

Examples of the alkali metal include lithium, sodium, and potassium, and sodium or potassium is preferred.

Examples of the basic amino acid residue include an arginine residue, a lysine residue, a histidine residue, and an ornithine residue.

Examples of the alkanolamine residue having a $C_{2-3}$ hydroxyalkyl group include a monoethanolamine residue, a diethanolamine residue, and a triethanolamine residue.

Examples of the aliphatic alkanolammonium include 2-amino-2-methyl-1-propanol and 2-amino-2-methyl-1,3-propanediol.

The compound having perfluoroalkyl groups in the present invention can be synthesized by known methods. For example, the compound can be synthesized through a two-step process in which a perfluoroalkylethanol is reacted with glutaconic acid in a solvent of toluene using p-toluenesulfonic acid as a catalyst, and then the obtained product is reacted with sodium hydrogen sulfite in dioxane.

The present invention also encompasses a water/supercritical carbon dioxide microemulsion including the surfactant.

When forming a water/supercritical carbon dioxide microemulsion, the surfactant commonly has a concentration of $10^{-10}$% by mol to $10^2$% by mol, $10^{-9}$ to 50% by mol, or $10^{-8}$ to 10% by mol, based on a molar amount of the supercritical carbon dioxide. The lower limit concentration of the surfactant may be a lowest concentration (called cμc) at which a microemulsion can be formed or more. For example, when the concentration is less than $10^{-10}$% by mol, a water/supercritical carbon dioxide microemulsion cannot be formed. The upper limit concentration of the surfactant may be a highest concentration at which the surfactant can form a microemulsion without forming a liquid crystal phase or can be dissolved in carbon dioxide or less. For example, when the concentration is higher than $10^2$% by mol, a liquid crystal phase may be formed or the surfactant may not be dissolved in carbon dioxide to form precipitates.

When forming a water/supercritical carbon dioxide microemulsion, the amount of water added (molar ratio of water ($W_0$)) is commonly 0.001 to 1,000 mol, 0.005 to 500 mol, or 0.01 to 200 mol, with respect to 1 mol of the surfactant under a condition with a temperature of 75° C. and a pressure of 30 MPa.

The action mechanism of the surfactant of the present invention is not completely clear in a W/scCO$_2$ μE. In particular, there is no completely satisfactory reason why though the surfactant of the present invention has perfluoroalkyl groups with a small number of carbon atoms, which are hydrophobic groups and provide carbon dioxide-philic properties, the surfactant in a W/scCO$_2$ μE can have a water dispersion ability almost equal to that of a fluorocarbon surfactant having longer perfluoroalkyl groups. However, the reason is suggested as follows.

The surfactant of the present invention, that is, the sulfoglutarate compound having $C_{1-7}$ perfluoroalkyl groups has an inverse cone stereostructure as with 8FG(EO)$_2$ having perfluorooctyl groups, which shows the highest water dispersion ability among previously reported surfactants. That is, it is supposed that two hydrophobic groups (perfluoroalkyl groups) are open while placing the hydrophilic group (sulfonic acid group) at the center, and the conformation stabilizes a W/scCO$_2$ μE having an inverse micelle structure.

Furthermore, in the case of 8FG(EO)$_2$ having perfluorooctyl groups, when the amount of water exceeds an upper limit capable of forming a W/scCO$_2$ μE, a precipitation phase (liquid crystal phase) of the surfactant appears. However, it is supposed that when the perfluoroalkyl group becomes shorter, a liquid crystal phase that interferes with W/scCO$_2$ μE formation is destabilized to maintain the W/scCO$_2$ μE state to the range of a higher ratio of water amount.

Then, it is supposed that such effect largely exceeds the negative effect that water dispersion ability is decreased (6FS(EO)$_2$: $W_0^c$=about 16) when the perfluoroalkyl group has a shorter carbon chain, as observed in 8FS(EO)$_2$ ($W_0^c$=about 32) that is a surfactant of a sulfosuccinate compound having perfluoroalkyl groups, and thus the surfactant of the present invention can provide the effect of the formation and the stabilization of a W/scCO$_2$ μE.

Furthermore, it is supposed that the perfluoroalkyl group having a shorter carbon chain changes mobility of the surfactant through the interface of water/supercritical carbon dioxide and balance of the amount of dissolved molecules between a water phase and a CO$_2$ phase. Thus, it is supposed that water dispersion rate becomes high, and the time required to form a W/scCO$_2$ μE is reduced from several tens of minutes in the case of 8FG(EO)$_2$ having perfluorooctyl groups to several seconds to several tens of seconds in the case of the surfactant of the present invention.

EXAMPLES

Hereinafter, the present invention will be described in further detail with reference to Examples, but the present invention is not limited to Examples.

Example 1

Preparation of Fluorocarbon Surfactant, 4FG(EO)$_2$

Synthesis of Intermediate of 4FG(EO)$_2$ (Bis(3,3,4,4,5,5,6,6,6-nonafluorohexyl)pent-2-enedioate)

Into a reaction flask, 4.0 g (16 mmol) of 3,3,4,4,5,5,6,6,6-nonafluorohexanol (manufactured by AZmax Co. Ltd., purity: 97%), 0.98 g (7.5 mmol) of glutaconic acid (manufactured by Fluka, purity: 97.0%), and 0.40 g (2.1 mmol) of p-toluenesulfonic acid monohydrate (manufactured by Wako Pure Chemical Industries, Ltd., purity: 99.0%) were placed, and 30 mL of toluene (manufactured by Wako Pure Chemical Industries, Ltd., purity: 99.5%) was added. The contents were dissolved, and stirred at 110° C. for 50 hours with a Dean-Stark apparatus while refluxing and dehydrating. The reaction mixture was cooled to room temperature. Then, to the reaction solution, 40 mL of an aqueous sodium hydrogen carbonate solution (prepared by dissolving a reagent powder manufactured by Wako Pure Chemical Industries, Ltd. in water: 1.84 mol/L) was added while cooling with ice water, and the whole was stirred at 25° C. for 10 minutes.

Then, the reaction solution was transferred into a separatory funnel, toluene (manufactured by Wako Pure Chemical Industries, Ltd., purity: 99.5%, 10 mL) was added as an organic phase, and the organic phase was separated. Next, the water phase was confirmed to be alkaline using a pH indicator paper. Then, calcium sulfate (manufactured by W.A. HAMMOND DRIERITE CO. LTD., DRIERITE [registered trademark], 10 to 20 mesh) was added to the organic phase for dehydration, and then calcium sulfate was removed by filtration. The obtained filtrate was concentrated under reduced pressure at 40° C. Then, column chromatography was carried out using silica gel (manufactured by Kanto Chemical Co., Inc., silica gel 60 (spherical), a particle diameter of 63 to 210 μm) dried under vacuum at 80° C. and a developing solvent (dichloromethane (manufactured by Wake Pure Chemical Industries, Ltd.), purity: 99.5%) previously dehydrated with calcium sulfate to give 3.4 g of an intermediate of 4FG(EO)$_2$ (bis(3,3,4,4,5,5,6,6,6-nonafluorohexyl)pent-2-enedioate) of Formula [A] below as an object (yield: 75%).

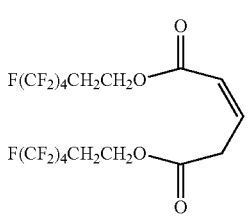

[A]

Synthesis of Fluorocarbon Surfactant: 4FG(EO)$_2$ (Sodium 1,5-bis((3,3,4,4,5,5,6,6,6-nonafluorohexyl)oxy)-1,5-dioxopentane-2-sulfonate)

Into a reaction flask, 2.2 g (3.5 mmol) of the intermediate of 4FG(EO)$_2$ of Formula [A] synthesized above and an aqueous sodium hydrogen sulfite solution in which 2.1 g of sodium hydrogen sulfite (manufactured by Wako Pure Chemical Industries, Ltd., purity: 64.0 to 67.4%) was dissolved in 10 mL of water were placed, and 20 mL of 1,4-dioxane (manufactured by Wako Pure Chemical Industries, Ltd., a purity >99.9%) was added. The whole was stirred at 100° C. for 48 hours. The reaction solution was concentrated under reduced pressure, and the precipitated solid was dried under vacuum. The solid was Soxhlet extracted using acetone (manufactured by Wako Pure Chemical Industries, Ltd., purity: 99.5%) previously dehydrated with calcium sulfate (manufactured by W.A. HAMMOND DRIERITE CO. LTD., DRIERITE [registered trademark], 10 to 20 mesh) for purification. The obtained solid was dried under vacuum. Then, the operation that the solid was added to dichloromethane (manufactured by Wako Pure Chemical Industries, Ltd., purity: 99.5%), and the whole was stirred while pulverizing particles and filtered was repeated several times. The particles were dried under vacuum to give 0.69 g of a fluorocarbon surfactant: 4FG(EO)$_2$ (sodium 1,5-bis((3,3,4,4,5,5,6,6,6-nonafluorodecyl)oxy)-1,5-dioxapentane-2-sulfonate) of Formula [B] below as a target compound (yield: 28%).

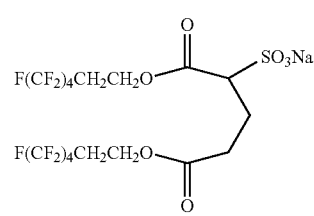

[B]

Comparative Example 1

Preparation of Fluorocarbon Surfactant, 8FG(EO)$_2$

Synthesis of Intermediate of 8FG(EO)$_2$ (Bis(1H,1H,2H,2H-perfluorodecyl)pent-2-enedioate)

As Comparative Example, a fluorocarbon surfactant having C$_8$ perfluoroalkyl groups: 8FG(EO)$_2$ was synthesized according to Non-patent Document 9.

Into a reaction flask, 30.0 g (65 mmol) of 1H,1H,2H,2H-perfluorodecanol (manufactured by AZmax Co. Ltd., purity: 97%), 4.3 g (34 mmol) of glutaconic acid (manufactured by Fluka, purity: 97.0%), and 1.2 g (6.3 mmol) of p-toluenesulfonic acid monohydrate (manufactured by Wako Pure Chemical Industries, Ltd., purity: 99.0%) were placed, and 120 mL of toluene (manufactured by Wako Pure Chemical Industries, Ltd., purity: 99.5%) was added. The contents were dissolved, and stirred at 115° C. for 24 hours with a Dean-Stark apparatus while refluxing and dehydrating. The reaction mixture was cooled to room temperature. Then, to the reaction solution, 40 mL of an aqueous sodium hydrogen carbonate solution (prepared by dissolving a reagent powder manufactured by Wako Pure Chemical Industries, Ltd. in water: 1.84 mol/L) was added while cooling with ice water, and the whole was stirred at 25° C. for 10 minutes.

Then, the reaction solution was transferred into a separatory funnel, and the organic phase was separated. Next, the water phase was confirmed to be alkaline using a pH indicator paper. Then, calcium sulfate (manufactured by W.A. HAMMOND DRIERITE CO. LTD., DRIERITE [registered trademark], 10 to 20 mesh) was added to the organic phase for dehydration, and then calcium sulfate was removed by filtration. The obtained filtrate was concentrated under reduced pressure at 40° C. Then, the unreacted alcohol was removed by distillation under reduced pressure (140° C.,<1 Torr), and the residual solid was recrystallized from ethanol to give 20.6 g of an intermediate of $8FG(EO)_2$ of Formula [C] below (bis(1H,1H,2H,2H-perfluorodecyl)pent-2-enedioate) (yield: 60.9%).

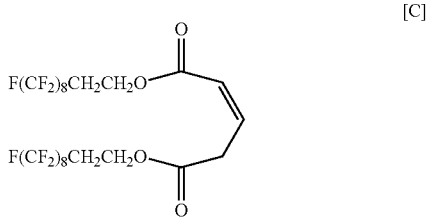

[C]

Synthesis of Fluorocarbon Surfactant: $8FG(EO)_2$ (Sodium 1,5-bis((1H,1H,2H,2H,-perfuluorodecyl)oxy)-1,5-dioxopentane-2-sulfonate)

Into a reaction flask, 20.6 g (20 mmol) of the intermediate of $8FG(EO)_2$ of Formula [C] synthesized above and an aqueous sodium hydrogen sulfite solution in which 6.5 g of sodium hydrogen sulfite (manufactured by Wako Pure Chemical Industries, Ltd., purity: 64.0 to 67.4%) was dissolved in 110 mL of water were placed, and 265 mL of 1,4-dioxane (manufactured by Wako Pure Chemical Industries, Ltd., a purity >99.9%) was added. The whole was stirred at 100° C. for 120 hours. The reaction solution was filtered, and the obtained solid was washed with 1,4-dioxane. The solid was Soxhlet extracted using acetone (manufactured by Wako Pure Chemical Industries, Ltd., purity: 99.5%) previously dehydrated with calcium sulfate (manufactured by W.A. HAMMOND DRIERITE CO. LTD., DRIERITE [registered trademark], 10 to 20 mesh) for purification. Acetone was removed by evaporation. The obtained solid was dried under vacuum, then washed with dichloromethane (manufactured by Wako Pure Chemical Industries, Ltd., purity: 99.5%) and toluene (manufactured by Wako Pure Chemical Industries, Ltd., purity: 99.5%), and dried under vacuum once again to give 5.3 g of a fluorocarbon surfactant: $8FG(EO)_2$ (sodium 1,5-bis((1H,1H,2H,2H-perfluorodecyl)oxy)-1,5-dioxopentane-2-sulfonate) of Formula [D] below (yield: 23.3%) as a target compound.

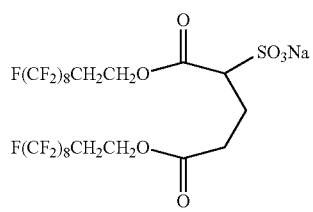

[D]

Example 2

Phase Behavior Observation of Water/Supercritical Carbon Dioxide/$4FG(EO)_2$ Mixture-1

An apparatus including a variable volume pressure-resistant cell (manufactured by Tama Seiki Ind. Co. Ltd., inner diameter: 24 mm) having a window for observing inside was assembled as shown in FIG. 1, and the phase behavior observation was carried out on a water/supercritical carbon dioxide/$4FG(EO)_2$ mixture.

In a piston front side area (window side) of the inside of the variable volume pressure-resistant cell, 264 mg (0.364 mmol) of the fluorocarbon surfactant: $4FG(EO)_2$ obtained in Example 1 was placed, and the cell was sealed. Then, the inside of the variable volume pressure-resistant cell was dried using a vacuum pump. The temperature was set at 35° C., and 20 g of carbon dioxide (manufactured by Nippon Ekitan Corporation, purity: 99.99% or more) ($4FG(EO)_2$ concentration (based on carbon dioxide): 0.08% by mol) was pressed into the piston front side area in the variable volume pressure-resistant cell. The temperature was increased to 75° C., and then the pressure was increased to 34.3 MPa (350 kgf/cm$^2$) in a piston rear side area of the variable volume pressure-resistant cell. The contents were stirred overnight to dissolve the fluorocarbon surfactant: $4FG(EO)_2$ into carbon dioxide, and the formation of a transparent homogeneous phase was visually confirmed. The pressure in the pressure-resistant cell shown below was controlled by increasing or decreasing the pressure of carbon dioxide in the piston rear side area in the variable volume pressure-resistant cell.

Next, the pressure in the pressure-resistant cell was gradually decreased from the homogeneous phase state. The pressure (hereinafter called phase boundary pressure) at which the inside of the variable volume pressure-resistant cell started clouding (the surfactant started precipitating and the contents became an inhomogeneous phase) was recorded from 75° C. to 35° C. at intervals of 10° C. (visually observed). A phase boundary pressure in this state is the limit pressure at which 0.08% by mol of $4FG(EO)_2$ can be dissolved in carbon dioxide.

Then, the phase boundary pressures were recorded to 35° C., and 60 µL of water was introduced into the variable volume pressure-resistant cell using a 6-port valve. The contents were stirred at 75° C. and 34.3 MPa (350 kgf/cm$^2$) until a transparent homogeneous phase was obtained.

The formation of a transparent homogeneous phase was visually confirmed; next, the pressure in the variable volume pressure-resistant cell was gradually decreased once again; then, the phase boundary pressure was recorded (from 75° C. to 35° C. at intervals of 10° C.); and then 60 µL of water was introduced into the cell. Such operation similar to the above was repeated. The operation was repeated until a homogeneous phase was not formed at 75° C. and 34.3 MPa (350 kgf/cm$^2$) and the data of the phase boundary pressure were collected. The homogeneous phase is a microemulsion phase when carbon dioxide contains water in an amount that could not be dissolved, the cloud phase appearing with pressure decrease is a macroemulsion phase, and the phase boundary pressure represents a boundary pressure between these phases.

Figure 2:
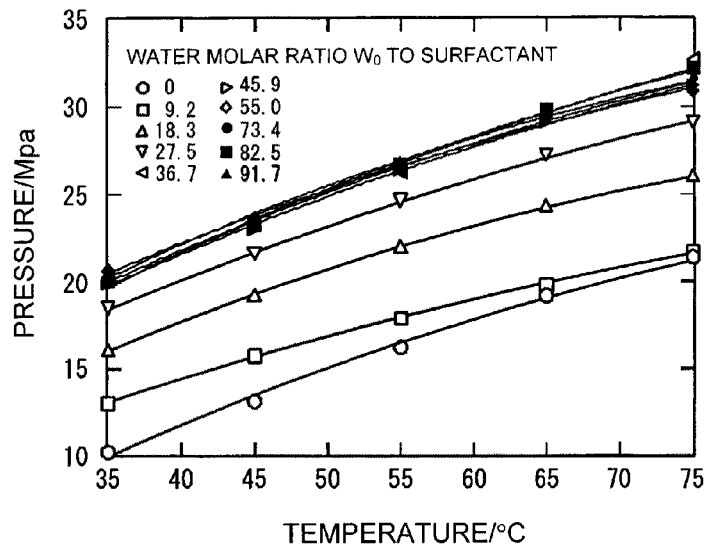
FIG. 2 is a view showing changes in phase boundary pressure with respect to temperature at each $W_0$ obtained in Example 2.

The molar ratio of water with respect to 1 mol of the surfactant ($4FG(EO)_2$) present in the measurement system is regarded as $W_0$, and the relation between phase boundary pressure and temperature at each $W_0$ is shown in Table 1 and FIG. 2. Under the condition where $W_0$ is more than 91.7, the formation of a microemulsion phase was not observed and only a precipitation phase in which a water phase was separated was observed in a temperature range from 35 to 75° C. and in a pressure range of 40 MPa or less.

Figure 3:
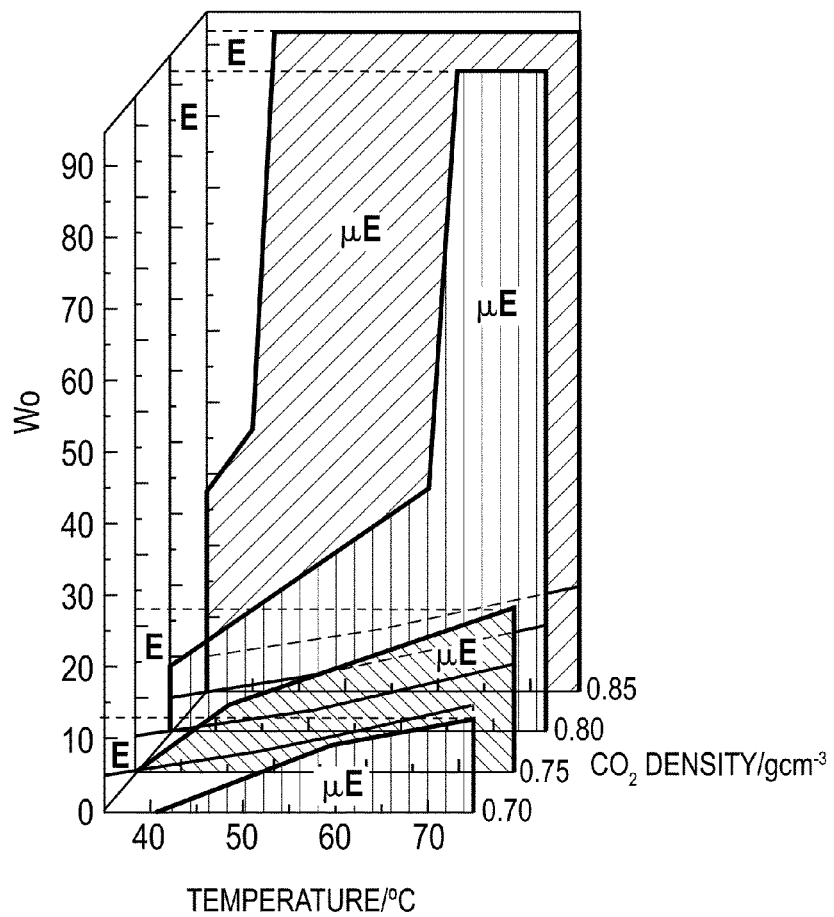
FIG. 3 is a phase diagram of the water/supercritical carbon dioxide/4FG(EO)$_2$ mixture obtained in Example 2 and shows relations of $W_0$ with respect to temperature and carbon dioxide density and solubility curves of water.

Furthermore, as a phase diagram of the water/supercritical carbon dioxide/4FG(EO)$_2$ mixture, the relations of $W_0$ with respect to the temperature and the carbon dioxide density are shown in FIG. 3. FIG. 3 also shows the solubility curve of water at each density of carbon dioxide. µE shown in Figure 5 means microemulsion. The formation of a microemulsion was confirmed in the region shown as µE, and a macroemulsion phase and a precipitation phase in which a water phase was separated were formed in other regions shown as E.

Furthermore, from the phase diagram of the water/supercritical carbon dioxide/4FG(EO)$_2$ mixture shown in FIG. 3, the formation of a microemulsion phase was confirmed in a wider range to a high $W_0$ value. The result is that the value is higher than that of the hydrocarbon surfactant (TMN-6), and the surfactant has a microemulsion forming ability in a wide range almost equal to that of the fluorocarbon surfactant: 8FG(EO)$_2$ (FIG. 4) that has the highest value until now and that is shown as Comparative Example.

TABLE 1

Relation between phase boundary pressure and temperature at each $W_0$

| Temperature | Pressure [MPa] Water amount (µL)/water molar ratio to surfactant ($W_0$) | | | | | | | | | | | |
|---|---|---|---|---|---|---|---|---|---|---|---|---|
| [° C.] | 0/0 | 60/9.2 | 120/18.3 | 180/27.5 | 240/36.7 | 300/45.9 | 360/55.0 | 420/64.2 | 480/73.4 | 540/82.5 | 600/91.7 | 660/100.9 |
| 75 | 21.4 | 21.7 | 26.0 | 29.1 | 32.7 | 31.2 | 30.9 | 34.5 | 31.4 | 32.2 | x | x |
| 65 | 19.2 | 19.8 | 24.3 | 27.2 | 29.6 | 29.1 | 29.3 | 31.5 | 29.3 | 29.8 | 29.7 | x |
| 55 | 16.2 | 17.9 | 22.0 | 24.6 | 26.2 | 26.4 | 26.6 | 28.2 | 26.5 | 26.7 | 26.8 | x |
| 45 | 13.1 | 15.7 | 19.2 | 21.6 | 23.2 | 23.0 | 23.6 | 25.0 | 23.4 | 23.2 | 23.5 | x |
| 35 | 10.2 | 13.0 | 16.1 | 18.5 | 20.2 | 19.9 | 20.6 | 21.4 | 20.1 | 20.0 | 20.5 | x | x: No microemulsion phase was formed.

Comparative Example 2

Phase Behavior Observation of Water/Supercritical Carbon Dioxide/8FG(EO)$_2$ Mixture-1

Figure 4:
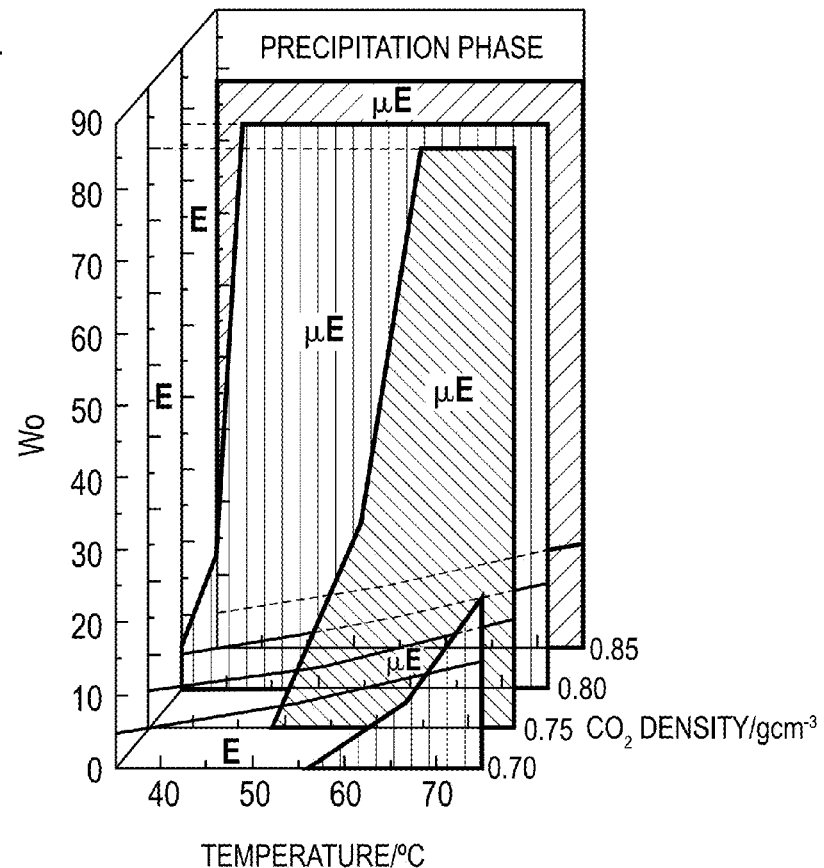
FIG. 4 is a phase diagram of the water/supercritical carbon dioxide/8FG(EO)$_2$ mixture obtained in Comparative Example 2 and shows relations of $W_0$ with respect to temperature and carbon dioxide density and solubility curves of water.

The phase behavior observation was carried out on a water/supercritical carbon dioxide/8FG(EO)$_2$ mixture by the method described in Example 2 except that 8FG(EO)$_2$ synthesized in Comparative Example 1 was used as a fluorocarbon surfactant. FIG. 4 shows the relations of $W_0$ with respect to the temperature and the carbon dioxide density as a phase diagram of the water/supercritical carbon dioxide/8FG(EO)$_2$ mixture. FIG. 4 also shows the solubility curve of water at each density of carbon dioxide.

As shown in Table 1, in a pressure range of 40 MPa or less, 4FG(EO)$_2$ prepared in Example 1 could well form a microemulsion, that is, $W_0$ was 91.7 (20.5 MPa) at 35° C., $W_0$ was 91.7 (23.5 MPa) at 45° C., $W_0$ was 91.7 (26.8 MPa) at 55° C., $W_0$ was 91.7 (29.7 MPa) at 65° C., and $W_0$ was 82.5 (32.2 MPa) at 75° C.

The microemulsion forming ability of a surfactant in supercritical carbon dioxide is expressed by $W_0^c$ that is obtained by subtracting the amount of water dissolved in carbon dioxide from $W_0$. The value subtracted from $W_0$ is commonly about 15 or less. Thus, the microemulsion forming ability of the fluorocarbon surfactant of the present invention: 4FG(EO)$_2$, $W_0^c$, becomes about 75. As a result, its microemulsion forming ability is very high in comparison with that of the known hydrocarbon surfactant, TMN-6 ($W_0^c$=about 20).

Furthermore, when compared with the fluorocarbon surfactant having $C_8$ perfluoroalkyl chains as a hydrophobic group: 8FG(EO)$_2$ ($W_0^c$=about 70), which is regarded to have the highest water dispersion ability (microemulsion forming ability) among previously reported surfactants, the surfactant of the present invention is supposed to have a lower water dispersion ability in conventional common knowledge of the technology because the perfluoroalkyl group has a smaller carbon atom number. However, the surfactant of the present invention actually had a water dispersion ability almost equal to that of 8FG(EO)$_2$.

Example 3

Phase Behavior Observation of Water/Supercritical Carbon Dioxide/4FG(EO)$_2$ Mixture-2

In a similar manner to that in Example 2, the phase behavior observation was carried out on a water/supercritical carbon dioxide/4FG(EO)$_2$ mixture using an apparatus assembled as in FIG. 1. In this system, the formation rate of a water/supercritical carbon dioxide microemulsion was evaluated by visual confirmation of the time required to form a homogeneous single phase when water was added under a certain condition.

In a piston front side area (window side) of the inside of the variable volume pressure-resistant cell, 264 mg (0.364 mmol) of the fluorocarbon surfactant: 4FG(EO)$_2$ obtained in Example 1 was placed, and the cell was sealed. Then, the inside of the variable volume pressure-resistant cell was dried using a vacuum pump. The temperature was set at 35° C., and 20 g of carbon dioxide (manufactured by Nippon Ekitan Corporation, purity: 99.99% or more) (4FG(EO)$_2$ concentration (based on carbon dioxide): 0.08% by mol) was pressed into a piston front side area of the variable volume pressure-resistant cell. The temperature was increased to 75° C., and then the pressure was increased to 34.3 MPa (350 kgf/cm$^2$) in the piston rear side area of the variable volume pressure-resistant cell. The contents were stirred overnight to dissolve 4FG(EO)$_2$ into carbon dioxide, and the formation of a transparent homogeneous phase was visually confirmed. From the homogeneous phase state, 60 µL of water was introduced into the pressure-resistant cell using a 6-port valve, and the formation of a transparent homogeneous phase was observed with time while stirring the contents at 75° C. and 34.3 MPa (350 kgf/cm$^2$). After confirming the formation of a homogeneous phase, 60 µL of water was introduced into the pressure-resistant cell once again using the 6-port valve, and the formation of a transparent homogeneous phase was observed with time while stirring the contents at 75° C. and 34.3 MPa (350 kgf/cm$^2$). Such operation was repeated, and the formation rate of a water/supercritical carbon dioxide microemulsion was evaluated,

Comparative Example 3

Phase Behavior Observation of Water/Supercritical Carbon Dioxide/8FG(EO)$_2$ Mixture-1

The phase behavior observation was carried out on a water/supercritical carbon dioxide/8FG(EO)$_2$ mixture by the method described in Example 3 except that 8FG(EO)$_2$ synthesized in Comparative Example 1 was used as a fluorocarbon surfactant, and the formation rate of a water/supercritical carbon dioxide microemulsion was evaluated.

Figure 5:
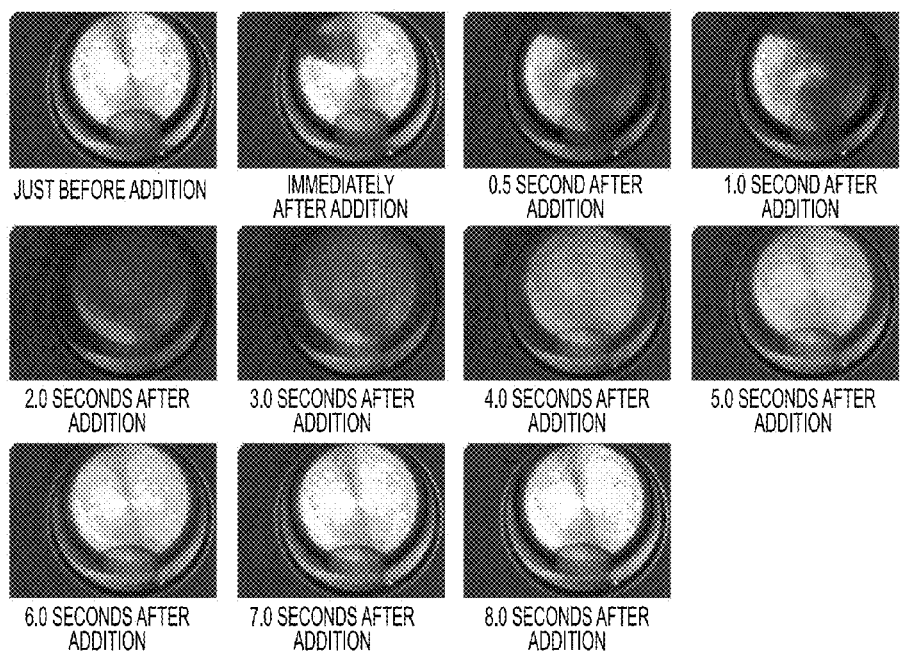
FIG. 5 is photographs showing a water/supercritical carbon dioxide/4FG(EO)$_2$ mixture with time from when water is added into carbon dioxide dissolving 4FG(EO)$_2$ obtained in Example 3 until a transparent homogeneous phase is obtained ($W_0$=74).

FIG. 5 shows photographs of the water/supercritical carbon dioxide/4FG(EO)$_2$ mixture with time from adding water into the pressure-resistant cell until obtaining a transparent homogeneous phase ($W_0$–74). When using the fluorocarbon surfactant of the present invention: 4FG(EO)$_2$, cloudiness was observed in the pressure-resistant cell because an inhomogeneous phase was formed immediately after adding water. However, after about 5 to 6 seconds, the cloudiness disappeared in the pressure-resistant cell and a transparent homogeneous phase was formed, that is, the formation of a microemulsion was observed. Moreover, the behavior of such rapid formation of a transparent homogeneous microemulsion after adding water into the system was also observed even when the amount of water added was increased, and when $W_0$ was 74 or less, the formation of a microemulsion was observed within several to 10 seconds after adding water into the system.

Usually, for example, when the hydrocarbon surfactant (TMN-6) is used, at least several tens of minutes are required from adding water into carbon dioxide dissolving the surfactant until water is completely dispersed (solubilized) to form a transparent homogeneous phase. Actually, in Comparative Example 3, in the case of the fluorocarbon surfactant having $C_8$ perfluoroalkyl chains as a hydrophobic group: 8FG(EO)$_2$, it was not until several tens of minutes after water was added into carbon dioxide dissolving the surfactant that the formation of a transparent homogeneous phase in which water was completely dispersed and solubilized was confirmed.

That is, when using the fluorocarbon surfactant of the present invention: 4FG(EO)$_2$, the transparent homogeneous phase was formed within about several to 10 seconds, and it was ascertained that the fluorocarbon surfactant has characteristics of very high formation rate of microemulsion.

Such characteristics are ascribable to high adsorbability to a W/scCO$_2$ interface and high interfacial tension decreasing ability of the fluorocarbon surfactant of the present invention: 4FG(EO)$_2$. Furthermore, such characteristics have an advantage in the development of continuous reaction processes using a W/scCO$_2$ μE.

Example 4

Phase Behavior Observation of Water/Supercritical Carbon Dioxide/4FG(EO)$_2$ Mixture-3

The phase behavior observation was carried out on a water/supercritical carbon dioxide/4FG(EO)$_2$ mixture using a spectrophotometer. In this system, methyl orange was used as a marker.

Into a pressure-resistant transmission spectroscopic cell having two quartz windows (manufactured by L. TEX Corporation, an optical length of 10 mm, an internal volume of 1.6 ml), 17 mg of the fluorocarbon surfactant: 4FG(EO)$_2$ obtained in Example 1 was sealed, and then carbon dioxide (manufactured by Nippon Ekitan Corporation, purity: 99.99% or more) was pressed into the cell under a condition of 75° C. until the pressure reached 35 MPa to prepare 0.085% by mol of a 4FG(EO)$_2$/supercritical carbon dioxide solution. Then, under the same temperature and pressure conditions, 40 μL of a 0.1% by weight aqueous methyl orange solution (prepared by dissolving methyl orange (powder, manufactured by Aldrich) in a predetermined amount of water) was introduced as a marker aqueous solution into the system using a 6-port valve, and the contents were stirred. When confirming the formation of a transparent homogeneous phase, a UV-Vis absorption spectrum was recorded at each $W_0$ using a spectrophotometer (manufactured by Hitachi High-Technologies Corporation, U-2810). Adding of 40 μL of the aqueous methyl orange solution, stirring of the contents, and recording of a UV-Vis absorption spectrum were repeated, and thus data were collected to $W_0$=190.4.

Figure 6:
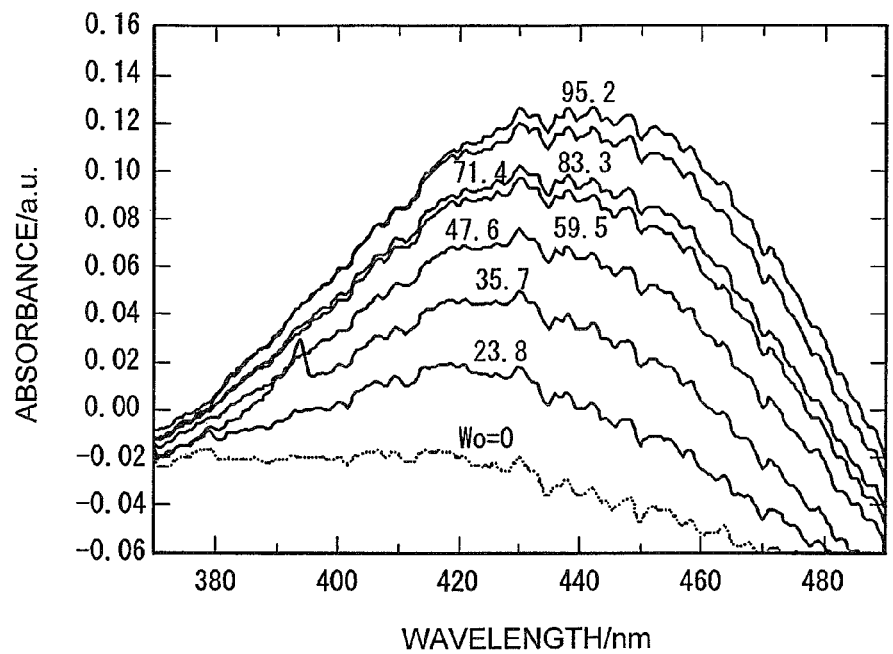
FIG. 6 is a view showing UV-Vis absorption spectra at each $W_0$ obtained in Example 4 ($W_0$=95.2 or less). In FIG, each number shows $W_0$ of each spectrum.
Figure 7:
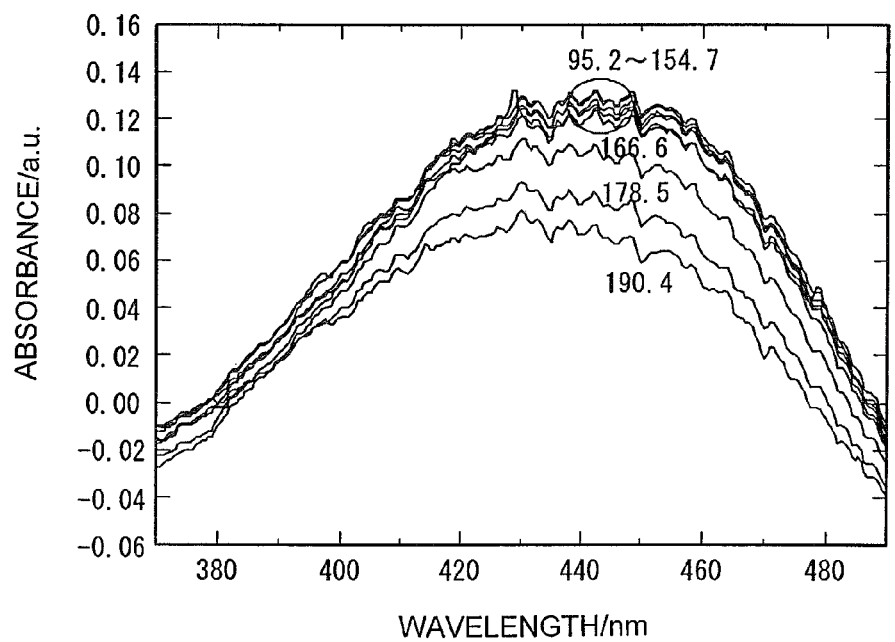
FIG. 7 is a view showing UV-Vis absorption spectra at each $W_0$ obtained in Example 4 ($W_0$=95.2 or more). In FIG, each number shows $W_0$ of each spectrum.

FIG. 6 and FIG. 7 show the UV-Vis absorption spectra at each $W_0$ (FIG. 6: $W_0$=95.2 or less, FIG. 7: $W_0$=95.2 or more). Though no absorption peak was observed in a range from 370 to 500 nm before introduction of the aqueous methyl orange solution ($W_0$=0), absorption appeared due to the methyl orange when the aqueous methyl orange solution was introduced, and the absorbance continued to increase to $W_0$–about 80 (FIG. 6). In contrast, the absorbance was slightly changed in a range of $W_0$=95.2 to 154.7, and tended to be gradually decreased at $W_0$–154.7 or more (FIG. 7). A transparent homogeneous phase was confirmed at each $W_0$ recorded, and no precipitation was visually observed.

Figure 8:
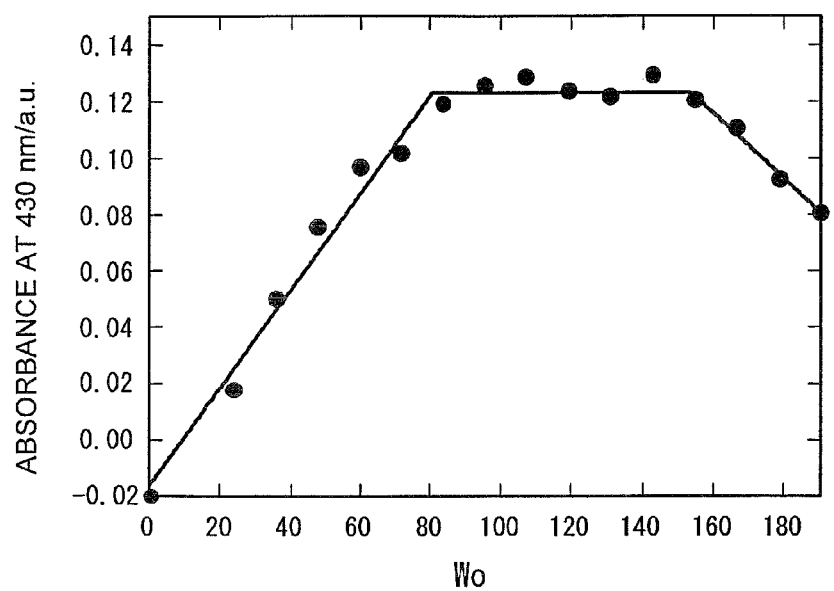
FIG. 8 is a view showing changes in absorbance at 430 nm in the UV-Vis absorption spectra with respect to $W_0$ obtained in Example 4.

FIG. 8 shows changes in absorbance at 430 nm in the UV-Vis absorption spectrum with respect to $W_0$. As described above, the absorbance increased in proportion to $W_0$ until $W_0$–80.5, and it was ascertained that the aqueous methyl orange solution added as a marker was incorporated into the inside of the microemulsion to be dispersed in carbon dioxide.

In contrast, the absorbance was slightly changed in $W_0$–80.5 to 150 and gradually decreased in $W_0$=150 or more. It is supposed that a Winsor-II microemulsion phase was formed because no precipitation was clearly observed visually. Here, the Winsor-II microemulsion phase means a phase in which excess water that is not incorporated (dispersed) into a microemulsion phase is separate from the microemulsion.

The test result also reveals that the fluorocarbon surfactant: 4FG(EO)$_2$ can certainly disperse water having $W_0$=about 80.5 ($W_0^c$=about 65) as a microemulsion.

The test result showed a slightly lower water dispersion ability (microemulsion forming ability) as compared with the result in Example 2 ($W_0$=82.5 (32.2 MPa) at 75° C.). This is ascribable to the effect of the presence of methyl orange used as a marker, and the W/scCO$_2$ microemulsion is supposed to be destabilized by methyl orange. Therefore, when using pure water as in Example 2, it is supposed that a microemulsion is formed to a higher $W_0$ ($W_0^c$).

INDUSTRIAL APPLICABILITY

The water/supercritical carbon dioxide microemulsion formed by the surfactant of the present invention is expected to be to be applied to various fields such as synthesis of particles and nanocapsules, dry-cleaning, and extraction of useful substances including metal ions and proteins. Therefore, the surfactant of the present invention is very useful in industry.

DESCRIPTION OF THE REFERENCE NUMERALS 1 personal computer
2 CCD camera
3 spectrophotometer
4 pump
5 6-port valve and 25 μL sample loop
6 variable volume pressure-resistant cell
7 window
8 stirrer
9 movable piston
10 pressure gauge
11 screw cylinder
12 $CO_2$ cylinder

RELATED ART DOCUMENTS

Patent Document

[Patent Document 1] Japanese Patent Application Publication No. JP-A-2004-315675

Non-Patent Documents

[Non-patent Document 1] *Hyomen* (Surface), 2002, Vol. 40, No. 10, 9-23
[Non-patent Document 2] "Nano Technology with Supercritical Fluids" edited by Tadafumi Adschiri, published by CMC Publishing in August 2004, Chapter 3, Section 5, Microemulsion and Nanomaterials
[Non-patent Document 3] Ind. Eng. Chem. Res., 2003, Vol. 42, 6348-6358
[Non-patent Document 4] Langmuir, 1999, 15, 6613-6615
[Non-patent Document 5] Langmuir, 1994, 10, 3536-3541
[Non-patent Document 6] Langmuir, 1997, 13, 6980-6984
[Non-patent Document 7] Langmuir, 2001, 17, 274-277
[Non-patent Document 8] Langmuir, 2003, 19, 220-225
[Non-patent Document 9] J. Supercrit. Fluids, 2010, 53, 131-136
[Non-patent Document 10] Oleoscience, 2010, Vol. 10, No. 5, 167-177

The invention claimed is:

1. A water/supercritical carbon dioxide microemulsion comprising a surfactant, wherein the surfactant has a concentration of $10^{-10}$% by mol to $10^2$% by mol based on a molar amount of the supercritical carbon dioxide and the surfactant comprises a compound of Formula(1):

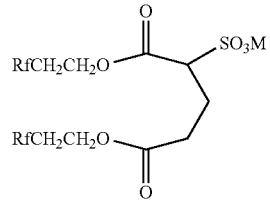

where Rf is a $C_{1-7}$ perfluoroalkyl group, M is a hydrogen atom, an alkali metal, ammonium, a basic amino acid residue, an alkanolamine residue having a $C_{2-3}$ hydroxyalklyl group, or aliphatic alkanolammonium.

2. The water/supercritical carbon dioxide microemulsion according to claim 1, wherein the amount of the water (molar ratio ($W_0$)) is 0.001 to 1,000 mol with respect to 1 mol of the surfactant under a condition with a temperature of 75° C. and a pressure of 30 MPa.

3. The water/supercritical carbon dioxide microemulsion according to claim 1, wherein the perfluoroalkyl group has a carbon atom number of to 6.

4. The water/supercritical carbon dioxide microemulsion according to claim 1, wherein the perfluoroalkyl group has a carbon atom number of 4.

5. The water/supercritical carbon dioxide microemulsion according to claim 1, wherein M is an alkali metal.

* * * * *